United States Patent
Rizkalla et al.

(10) Patent No.: US 7,553,980 B2
(45) Date of Patent: Jun. 30, 2009

(54) PROCESS FOR INITIATING A HIGHLY SELECTIVE ETHYLENE OXIDE CATALYST

(75) Inventors: Nabil Rizkalla, Rivervale, NJ (US);
Barry Jay Billig, Irvington, NY (US);
Norma B. Castagnola, East Windsor, NJ (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 0 days.

(21) Appl. No.: 11/861,736

(22) Filed: Sep. 26, 2007

(65) Prior Publication Data

US 2009/0082584 A1 Mar. 26, 2009

(51) Int. Cl.
*C07D 301/10* (2006.01)

(52) U.S. Cl. .................. 549/536; 549/537; 502/415

(58) Field of Classification Search .......... 549/537, 549/536; 502/415
See application file for complete search history.

(56) References Cited

U.S. PATENT DOCUMENTS

| | | | |
|---|---|---|---|
| 3,563,914 A | 2/1971 | Wattimena | |
| 3,702,259 A | 11/1972 | Nielsen | |
| 4,761,394 A | 8/1988 | Lauritzen | |
| 4,766,105 A | 8/1988 | Lauritzen | |
| 4,874,879 A | 10/1989 | Lauritzen et al. | |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,155,242 A | 10/1992 | Shankar et al. | |
| 5,187,140 A | 2/1993 | Thorsteinson et al. | |
| 5,407,888 A | 4/1995 | Herzog et al. | |
| 5,801,259 A * | 9/1998 | Kowaleski | 549/536 |
| 7,102,022 B2 | 9/2006 | Evans et al. | |
| 2004/0049061 A1 | 3/2004 | Lockemeyer et al. | |
| 2004/0171852 A1 | 9/2004 | Chipman et al. | |
| 2007/0208186 A1 | 9/2007 | Lockmeyer | |

* cited by examiner

*Primary Examiner*—David E. Gallis
*Assistant Examiner*—Nizal S. Chandrakumar
(74) *Attorney, Agent, or Firm*—Scully, Scott, Murphy & Presser, P.C.

(57) ABSTRACT

A process for initiating a highly selective ethylene oxide catalyst is provided in which the highly selective ethylene oxide catalyst is operated first as a 'standard' Ag-based catalyst (e.g., a catalyst that contains only silver and alkali metal, especially cesium). Moreover, the inventive initiation procedure is more efficient when the concentration of carbon dioxide in the feed is higher than 6 vol. %, and even more efficient when the concentration of carbon dioxide in the feed is higher than 10 vol. %, of the feed mixture during the initiation period.

14 Claims, No Drawings

PROCESS FOR INITIATING A HIGHLY SELECTIVE ETHYLENE OXIDE CATALYST

FIELD OF THE INVENTION

The present invention relates to the production of ethylene oxide utilizing a highly selective silver (Ag)-based catalyst. More particularly, the present invention relates to a start-up process that can be used to initiate a high selectivity Ag-based catalyst. The present invention also provides a process for the epoxidation of ethylene oxide utilizing the initiated high selectivity Ag-based catalyst of the present invention.

BACKGROUND OF THE INVENTION

In the catalytic oxidation of ethylene to ethylene oxide, the start-up operation of a highly selective Ag-based catalyst requires a special procedure. Specifically, the catalyst, especially when rhenium is used as a promoter, requires an initiation period before it is able to give the expected higher performance.

U.S. Pat. No. 4,874,879 to Lauritzen et al. and U.S. Pat. No. 5,155,242 to Shanker et al. disclose start-up processes in which freshly prepared rhenium (Re)-containing Ag-based catalysts are chlorinated before adding oxygen to the feed. That is, the '879 and the '242 patents disclose a start-up process in which the catalysts are pre-chlorinated prior to the introduction of oxygen into the feed. In particular, the catalysts were, initially, pre-chlorided with a feed containing ethylene, methane and ethyl chloride. This was followed by the addition of oxygen to the feed, at which time the reaction temperature was kept below 273° C. Eventually several adjustments to the reaction conditions were made in order to obtain an optimum performance. This prior art pre-chloriding step reportedly provided enhanced activity of the Re-containing catalysts and allowed the ethylene oxide reaction to start-up at low temperatures.

A further start-up process is disclosed in U.S. Patent Application Publication No. 2004/0049061 A1 to Lockemeyer et al. In particular, this disclosure provides a method for improving the selectivity of a supported highly selective epoxidation catalyst comprising Ag in a quantity of at most 0.17 g per $m^2$ surface area of the support. The improvement was achieved by contacting the catalyst with a feed including oxygen at a catalyst temperature above 250° C. for duration of up to, at most, 150 hours.

A yet further start-up process is disclosed in U.S. Pat. No. 7,102,022 to Lockemeyer et al. Specifically, the '022 patent discloses a method for the start-up of a process for the epoxidation of an olefin comprising an Ag-based highly selectivity epoxidation catalyst. The method disclosed in the '022 patent includes contacting a catalyst bed with a feed comprising oxygen. In this treatment, the temperature of the catalyst bed was above 260° C. for a period of time of, at most, 150 hours.

Despite the above start-up procedures, and because of the importance for operating Ag-based highly selective catalysts under optimum performance conditions, there is a continued need to develop new and improved methods that can be used for the start-up of a process for the epoxidation of olefins, especially ethylene.

SUMMARY OF THE INVENTION

The present invention provides a process for initiating a highly selective epoxidation catalyst. In particular, the applicants have determined that the 'activation' of a highly selective Ag-based catalyst, especially one including rhenium, Re, as a promoter, can be achieved if the catalyst is operated first as a 'standard' Ag-based catalyst. The term 'standard Ag-based catalyst' is used throughout the present application to denote a non-Re-containing catalyst that contains primarily silver and an alkali metal, especially cesium, Cs.

More specifically, it has been determined by the applicants that the inventive activation described above is more efficient when the concentration of carbon dioxide in the feed is greater than about 6 vol. % and even more efficient when the concentration of carbon dioxide in the feed is greater than about 10 vol. %, during the activation period. When the reaction conditions, especially the feed composition, are similar to those used in the start-up of a standard Ag-based catalyst, the catalyst is capable of operating at a higher work rate and the catalyst selectivity is in the range from about 80% to about 84%. By "higher work rate" it is meant the production of from about 50 to about 350 Kg ethylene oxide per $m^3$ of catalyst per hour, in particular from about 100 to about 300 Kg ethylene oxide per $m^3$ of catalyst per hour.

In the present invention, the initiation of the highly selective Ag-based catalyst is based on controlling the activity of the catalyst via introducing a gas feed that includes a high carbon dioxide concentration. Specifically, and in other words, the method of the present invention builds up the carbon dioxide in the feed to allow the reaction temperature to be increased while controlling the ethylene conversion in the reactor.

In general terms, a method for the start-up of a process for the epoxidation of ethylene is provided which comprises:

contacting a catalyst bed including a silver-based highly selective epoxidation catalyst with a feed gas composition at a first temperature, said feed gas composition including ethylene, oxygen, a moderator and carbon dioxide, said carbon dioxide is present in said feed gas composition in a concentration of greater than about 6 vol. %;

increasing the first temperature to a second temperature to produce a desired concentration of ethylene oxide; and adjusting the feed gas composition in order to maintain said desired concentration of ethylene oxide while achieving a desired catalyst work rate and selectivity.

In one embodiment of the present invention, the carbon dioxide concentration in the feed gas is greater than about 10 vol. %.

In another embodiment of the present invention, the silver-based highly selective epoxidation catalyst comprises a support, a catalytically effective amount of silver or a silver-containing compound, a promoting amount of rhenium or a rhenium-containing compound, and a promoting amount of one or more alkali metals or alkali-metal-containing compounds.

Preferably, the support comprises alumina, charcoal, pumice, magnesia, zirconia, titania, kieselguhr, fuller's earth, silicon carbide, silica, silicon dioxide, magnesia, clays, artificial zeolites, natural zeolites, ceramics or combinations thereof. More preferably, the support contains primarily alpha-alumina and has a surface area from 0.1 to 10 $m^2/g$.

The catalyst employed in the present invention further comprises a promoting amount of one or more Group IIA metal-containing compounds, one or more transition metal-containing compounds, one or more sulfur-containing compounds, one or more fluorine-containing compounds, one or more phosphorus-containing compounds, one or more boron-containing compounds, or combinations thereof.

When a Group IIA metal-containing compound is present, it typically comprises beryllium, magnesium, calcium, strontium, barium or combinations thereof. When a transition metal-containing compound is present, it comprises an element selected from Groups IVA, VA, VIA, VIIA and VIIIA of the Periodic Table of the Elements, or combinations thereof. Preferably, the transition metal-containing compound comprises molybdenum, tungsten, chromium, titanium, hafnium, zirconium, vanadium, thorium, tantalum, niobium or combinations thereof, with transition metal-containing compounds comprising molybdenum or tungsten or combinations thereof being more preferred.

The alkali metal-containing compound present in the catalyst comprises lithium, sodium, potassium, rubidium, cesium or combinations thereof, with cesium and lithium being more preferred.

The inventive epoxidation method includes the steps of:
contacting a catalyst bed including a silver-based highly selective epoxidation catalyst with a feed gas composition at a first temperature, said feed gas composition including ethylene, oxygen, a moderator and carbon dioxide, said carbon dioxide is present in said feed gas composition in a first concentration of greater than about 6 vol. %;
increasing the first temperature to a second temperature to produce a desired concentration of ethylene oxide;
adjusting the feed gas composition in order to maintain said desired concentration of ethylene oxide while achieving a desired catalyst work rate; and
lowering the second temperature to a third temperature, while simultaneously lowering the carbon dioxide concentration to a second concentration of about 5 vol. % or less, and more preferably 2 vol. % or less.

DETAILED DESCRIPTION OF THE INVENTION

As stated above, the prior art has disclosed that the start-up of a highly selective silver-based catalyst for ethylene oxidation requires a special procedure. This includes heating the catalyst at a high temperature, in excess of 250° C., for a period of up to 150 hours. During this "activation" the catalyst is not in a productive phase, or its productivity is at a specially limited level. The applicants have discovered that the "activation" of the highly selective silver-based catalyst, especially if it comprises Re as a promoter, could be easily achieved if the catalyst is operated first as a standard silver-based catalyst. The standard silver-based catalyst is a catalyst that contains only silver and an alkali metal, especially cesium.

Moreover, the applicants have determined that the inventive activation process is more efficient when the concentration of carbon dioxide in the feed is greater than about 6 vol. % and even more effective when it is greater than about 10 vol. %, of the feed mixture during the activation period. When the reaction conditions, especially the feed composition, are similar to those used in the start-up of a standard silver-based catalyst, the performance of the catalyst will be similar to that of the standard silver-based catalyst, e.g., the catalyst will be capable to operate at a higher work rate and its selectivity will be in the 80-84% range.

Before further describing the inventive start-up procedure, a description of the high selectivity catalyst that can be employed in the present invention is now provided. The high selectivity catalyst employed in the present invention is any silver-based supported catalyst which achieves a selectivity that is greater than 83%. The support employed in this invention may be selected from a large number of solid, refractory supports that may be porous. The support may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. A preferred support is comprised of alpha-alumina having a very high purity; i.e., at least 95 wt. % pure, or more preferably, at least 98 wt. % alpha-alumina. The remaining components may include inorganic oxides other than alpha-alumina, such as silica, alkali metal oxides (e.g., sodium oxide) and trace amounts of other metal-containing or non-metal-containing additives or impurities.

The support may be made utilizing conventional techniques well known to those skilled in the art. Alternatively, the support may be purchased from a catalyst support provider.

The support is preferably porous and has a B.E.T. surface area of at most 20 $m^2/g$, preferably from 0.1 to 10 $m^2/g$, and more preferably from 0.5 to 5 $m^2/g$. As used herein, the B.E.T. surface area is deemed to have been measured by the method as described in Brunauer, Emmet and Teller in J. Am. Chem. Soc, 60 (1938) 309-316. The support may have a monomodal pore size distribution or a multi-modal pore size distribution.

Regardless of the character of the support used, it is usually shaped into particles, chunks, pieces, pellets, rings, spheres, wagon wheels, cross-partitioned hollow cylinders, and the like, of a size suitable for employment in fixed-bed epoxidation reactors. Desirably, the support particles may have equivalent diameters in the range from about 3 mm to about 12 mm and preferably in the range from about 5 mm to about 10 mm, which are usually compatible with the internal diameter of the tubular reactors in which the catalyst is placed. Equivalent diameter is the diameter of a sphere having the same external surface (i.e., neglecting surface within the pores of the particle) to volume ratio as the support particles being employed.

In order to produce a catalyst for the oxidation of ethylene to ethylene oxide, a support having the above characteristics is then provided with a catalytically effective amount of silver on its surface. The catalyst is prepared by impregnating the support with a silver compound, complex or salt dissolved in a suitable solvent. Preferably, an aqueous silver solution is used. After impregnation, the excess solution is removed from the impregnated support, and the impregnated support is heated to evaporate the solvent and to deposit the silver or silver compound on the support as is known in the art.

Preferred catalysts prepared in accordance with this invention contain up to about 45% by weight of silver, expressed as metal, based on the total weight of the catalyst including the support. The silver is deposited upon the surface and throughout the pores of a porous refractory support. Silver contents, expressed as metal from about 1% to about 40% based on the total weight of the catalyst are preferred, while silver contents from about 8% to about 35% are more preferred. The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide. Useful silver containing compounds which are silver precursors non-exclusively include silver nitrate, silver oxide, or a silver carboxylate, e.g., silver oxalate, silver citrate, silver phthalate, silver lactate, silver propionate, silver butyrate and higher fatty acid salts and combinations thereof.

Also deposited on the support, either prior to, coincidentally with, or subsequent to the deposition of the silver is a promoting amount of a rhenium component, which may be a rhenium-containing compound or a rhenium-containing complex. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Also deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of silver, support, alkali metal promoters, rhenium component, and optional additional promoters of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity. In the epoxidation process, it may be desirable to intentionally change the operating conditions to take advantage of certain catalytic properties even at the expense of other catalytic properties. The preferred operating conditions will depend upon, among other factors, feedstock costs, energy costs, by-product removal costs and the like.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 10 parts per million to about 1000 parts per million, preferably from about 20 parts per million to about 500 parts per million, and more preferably from about 30 parts per million to about 350 parts per million of total catalyst expressed as the metal. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include a diamino alkane having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver. When a solvent is used, it may be an organic solvent or water, and may be polar or substantially non-polar. In general, the solvent should have sufficient solvating power to solubilize the solution components. At the same time, it is preferred that the solvent be chosen to avoid having an undue influence on, or interaction with, the solvated promoters.

The concentration of silver in the impregnating solution is typically in the range from about 1.0% by weight up to the maximum solubility afforded by the particular solvent/solubilizing agent combination employed. It is generally very suitable to employ solutions containing from about 5% to about 45% by weight of silver, with concentrations of from about 10 to about 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. A single impregnation or a series of impregnations, with or without intermediate drying, may be used, depending, in part, on the concentration of the silver component in the solution. Impregnation procedures are described in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, rhenium component, alkali metal component, and the optional other promoters, the impregnated support is calcined for a time sufficient to convert the silver containing compound to silver and to remove the volatile components from the impregnated support to result in a catalyst precursor. The calcination may be accomplished by heating the impregnated support, preferably at a gradual rate, to a temperature in the range from about 200° C. to about 600° C., preferably from about 200° C. to about 500°

C., and more preferably from about 200° C. to about 450° C., at a pressure in the range from 0.5 to 35 bar. In general, the higher the temperature, the shorter the required heating period. A wide range of heating periods have been suggested in the art; e.g., U.S. Pat. No. 3,563,914 suggests heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver compound is converted to silver. Continuous or step-wise heating may be used for this purpose.

During calcination, the impregnated support may be exposed to a gas atmosphere comprising an inert gas or a mixture of an inert gas with from about 10 ppm to about 21% by volume of oxygen.

After calcining the high selectivity catalyst, the calcined catalyst is loaded into reactor tubes of an epoxidation reactor, typically a fixed bed, tubular reactor, utilizing conventional loading methods well known to those skilled in the art. After loading, the catalyst bed may be swept by passing an inert gas such as nitrogen over the catalyst bed.

The inventive start-up procedure is now performed. In the instant invention, the initiation of the highly selective silver catalyst is based on controlling the activity of the catalyst via introducing a gas feed that includes a high concentration of carbon dioxide. In other words, it is desirable to build up the carbon dioxide in the feed to allow the reaction temperature to be increased while controlling the ethylene conversion across the reactor. Such a build up of carbon dioxide is typically required since a plant designed for high selectivity catalyst is normally designed for a feed containing low carbon dioxide concentration, e.g., 2% or less. For this type of plant design, the recycle gas is normally scrubbed of most of the produced carbon dioxide, as a reaction byproduct. Therefore, it may be necessary to modify the method of operation of the carbon dioxide removal system to achieve higher carbon dioxide levels in the gas feed, in the initiation phase of the fresh catalyst. The modification of the carbon dioxide removal system may include at least one of the following means:

1. A portion of the gas flow to the carbon dioxide absorber is by-passed.
2. A portion of the lean carbonate flow is by-passed.
3. The steam flow to the carbonate regenerator will be reduced to reduce the available carbonate in the lean carbonate solution for absorption of the carbon dioxide.

Using one or any combination of the three methods, the carbon dioxide concentration in the ethylene oxide reactor feed gas can be controlled to the desired high concentration.

The method of the present invention includes first contacting a catalyst bed including a silver-based highly selective epoxidation catalyst with a feed gas composition at a first temperature (typically from about 180° C. to about 220° C.). The feed gas composition includes ethylene, oxygen, a moderator, preferably a chloride-containing compound, and carbon dioxide. The carbon dioxide is present in said feed gas composition in a concentration of greater than about 6 vol. %, preferably greater than about 10 vol. %.

After a certain period of time (typically from about 1 to about 12 hours), the first temperature is increased to a second temperature (typically about 230° C. to about 270° C.) to produce a desired concentration of ethylene oxide and after a certain period of time, the feed gas composition is adjusted in order to maintain the desired concentration of carbon dioxide while achieving a desired catalyst work rate and selectivity. During the activation period, the desired concentration of carbon dioxide is typically greater than about 6 vol. % and it is even more efficient when the concentration of carbon dioxide in the feed is greater than about 10 vol. %. Also in this period, the desired work rate is from about 50 to about 350 Kg ethylene oxide per $m^3$ of catalyst per hour, in particular from about 100 to about 300 Kg ethylene oxide per $m^3$ of catalyst per hour, and most preferably from about 150 to about 250 Kg ethylene oxide per $m^3$ of catalyst per hour.

In one embodiment of the present invention, the feed composition during the activation period will be based on from about 5 to about 30% ethylene, from about 2 to about 8% oxygen, from about 6 to about 30% carbon dioxide and from about 0.2 to about 3.5 parts per million of effective chloride concentration.

The reaction conditions for the early phase of the start-up of the catalyst will resemble those that are normally used in the start-up of a standard catalyst. This includes the gradual increase of the concentration of the active components of the feed or the moderator. For instance, the start-up process disclosed in U.S. Pat. No. 4,874,879 to Lauritzen et al., e.g., pre-chloride the catalyst, or any alternative scheme for starting up a standard silver-based catalyst can be used in the present invention. When all the components of the feed are present in the specified levels, the selectivity of the catalyst will improve over the course of one or two days and will be stabilized at the performance expected from the standard catalyst.

In the prior art it is clearly stated that high levels of carbon dioxide, in the feed, is undesirable. For instance in U.S. Pat. No. 7,102,022, it is stated "Carbon dioxide is a by-product in the epoxidation process. However, carbon dioxide generally has an adverse effect on the catalyst activity, and high concentrations of carbon dioxide are therefore typically avoided". Contrary to this prior art, the carbon dioxide concentration is used in the present invention to control the catalyst activity and achieve full activation. Therefore, the feed composition has to be adjusted in order to achieve that control. With the present invention, i.e., activation at higher $CO_2$ level, the activity of the catalyst is curbed, and the needed temperature, for activation, will be safely achieved, without damaging the catalyst.

Initially, in the activation phase, the performance of the catalyst will improve at a fast rate. After 30-40 hours the catalyst will give the "standard catalyst" performance, e.g., selectivity at 78% or higher. The value of selectivity is expressed in the number of moles of ethylene oxide produced per 100 moles of ethylene consumed in the reaction.

Still for the next few days, the catalyst shows more improvement, though at a slower rate. This phase, of operating the catalyst as a standard catalyst, will last until the performance totally stabilizes. This will take additional 120-240 hours. The duration of this period will be a function of the temperature used in the activation. The temperature of the activation (herein claimed as the second temperature) will vary from about 230° C. to about 270° C., preferably from about 240° C. to about 255° C.

For starting up the fresh highly selective silver catalyst in a commercial plant is to first heat the catalyst up to a first temperature from about 180° C. to about 220° C. and pressurize the recycle loop to the ethylene oxide reactor with ethylene and a suitable ballast gas such as methane or nitrogen. Then, oxygen is slowly introduced to get the reaction started. The oxygen concentration in the feed is up to about 1% and preferably it is from about 0.2 to about 0.5%. This is followed by gradually introducing the moderator, a chlorohydrocarbon compound. The produced heat of the reaction is typically sufficient to raise the temperature as required to obtain a given conversion level.

Initially all the oxygen in the feed is consumed and the reactor effluent will virtually have no oxygen. The chlorohydrocarbon moderator is added slowly over a period of several hours until the oxygen break through, i.e., the effluent gas will contain some oxygen. The moderator is absorbed by the catalyst until the catalyst reaches a steady state at which point the catalyst will be less active and more selective, hence the presence of oxygen in the effluent. Suitable chloro-hydrocarbons, used as moderators, comprise chloro-hydrocarbons containing 1 to 6 carbon atoms. Preferably, the chloro-hydrocarbon is a chlorided ethane or a chlorided ethylene, e.g., ethyl chloride, ethylene dichloride, vinyl chloride or mixtures thereof. For the chloride level at this stage, it is preferred to add 0.2 to 3.0 ppm, by volume.

After the oxygen breakthrough, the level of oxygen to the recycle feed stream is then increased to a range from about 5 to about 40% of design rate. Reaction initiation will occur within a few minutes of the addition of the oxygen. After this, the components of the gas feed and the gas feed rate are raised to approximately the design conditions over a period of time ranging from about 15 minutes to several hours. For this stage of the catalyst initiation, the design conditions are typically:

| Feed Composition | 8-30% | ethylene |
| --- | --- | --- |
| | 2-8% | oxygen |
| | 6-30% | Carbon dioxide |
| | 0.2-3.5 ppm | moderator |
| | Balance | Inert gas |
| Ethylene oxide in effluent | 1-3% | |
| Selectivity | 79-85% | |
| GHSV | 3000-8000 | |
| Reaction pressure | 200-400 psig | |
| Reaction temperature | 230-260° C. | |

The preferred design conditions for the catalyst initiation stage are typically:

| Feed Composition | 10-25% | Ethylene |
| --- | --- | --- |
| | 5-7% | Oxygen |
| | 10-20% | Carbon dioxide |
| | 0.5-1.0 ppm | Moderator |
| | Balance | Inert gas |
| Ethylene oxide in effluent | 1.8-2.5% | |
| Selectivity | 82-84% | |
| GHSV | 3500-5000 | |
| Reaction pressure | 250-350 psig | |
| Reaction temperature | 240-250° C. | |

After adjusting the feed composition to contain the designed level of ethylene, oxygen and the moderator, the carbon dioxide level is allowed to build up to a concentration of greater than about 6 vol. %, preferably greater than about 10 vol. % or higher. This is followed by increasing the temperature to increase the level of ethylene oxide in the effluent gas, up to the designed rate. The catalyst is initially too active and it may be difficult to achieve the designed rate at the desired temperature. This high activity is controlled by allowing the carbon dioxide level to build up to a higher level in order to increase the reaction temperature without increasing the ethylene oxide level beyond the desired safe range.

With the gradual build up of the $CO_2$ level, the temperature of the reaction is raised to at least 230° C., preferably 240° C. and most preferably to at least 245° C. The catalyst's work rate and temperature are maintained at a fixed level for at least 100 hours, most preferably at least 160 hours, via adjusting the concentration of carbon dioxide in the feed. Through that period the catalyst's selectivity will increase to a range of 82-85%. For that period of catalyst "initiation" the plant is producing ethylene oxide at, or near to, the plant design capacity.

Since the idea of this procedure is to maintain plant production's capacity through the "initiation" period, ethylene oxide productivity has to be maintained at a constant level, along with a constant reaction temperature. Ethylene oxide production at a higher level than the design level, 1.5-3.0% in the reactor's effluent, is controlled by increasing the concentration of carbon dioxide in the feed. On the other hand, ethylene oxide production at a lower level than the design is controlled by increasing the concentration of ethylene in the feed, to bring it closer to the design value and/or reducing the concentration of $CO_2$, via removing a higher amount in the $CO_2$ absorber, the contactor.

After this catalyst initiation period, it is preferred to first lower the catalyst's temperature to 225° C. while simultaneously lowering the carbon dioxide concentration to a level of about 5 vol. % or less, preferably 2 vol. % or less, and maintaining the design ethylene oxide production rate and then optimize the moderator level to attain the high selectivity.

Another advantage of utilizing high level of carbon dioxide to control the catalyst's activity is that its effect is totally reversible. In other words, after the initiation period the catalyst's temperature is lowered and the concentration of carbon dioxide in the feed is reduced to that of the design level, less than 5 vol. %, there will be no adverse effect of using the higher level of $CO_2$ in the catalyst's initiation.

The epoxidation process, which occurs after the inventive start-up procedure, may be carried out by continuously contacting an oxygen-containing gas with ethylene, in the presence of the initiated catalyst produced by the invention. By way of example, reactant feed mixtures may contain from about 0.5% to about 45% ethylene and from about 3% to about 15% oxygen, with the balance comprising comparatively inert materials including such substances as carbon dioxide, inert gases, other hydrocarbons, and one or more reaction modifiers such as organic halides. Non-limiting examples of inert gases include nitrogen, argon, helium and mixtures thereof Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum. Non-limiting examples of reaction moderators include organic halides such as $C_1$ to $C_8$ halohydrocarbons. Preferably, the reaction moderator is methyl chloride, ethyl chloride, ethylene dichloride, ethylene dibromide, vinyl chloride or mixtures thereof. Most preferred reaction moderators are ethyl chloride and ethylene dichloride. Usually such reaction moderators are employed in an amount from about 0.3 to about 20 ppmv, and preferably from about 0.5 to about 15 ppmv of the total volume of the feed gas.

A usual method for the ethylene epoxidation process comprises the vapor-phase oxidation of ethylene with molecular oxygen, in the presence of the inventive initiated catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long filled with catalyst. Such reactors include a reactor outlet which allows the ethylene oxide, un-used ethylene, and byproducts to exit the reactor chamber.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 0.1 to about 5 seconds. The present initiated catalysts are effective for this process when operated within these ranges of conditions.

The resulting ethylene oxide, which exits the reactor through a reactor outlet, is separated and recovered from the reaction products using conventional methods. For this invention, the ethylene epoxidation process may include a gas recycle wherein substantially all of the reactor effluent is readmitted to a reactor inlet after substantially or partially removing the ethylene oxide product and the byproducts including carbon dioxide and water. In the recycle mode, carbon dioxide concentrations in the gas inlet to the reactor may be, for example, from about 0.3 to about 5 volume percent.

The catalysts initiated by the present invention have been shown to be particularly selective for oxidation of ethylene with molecular oxygen to ethylene oxide especially at high ethylene and oxygen conversion rates. The conditions for carrying out such an oxidation reaction in the presence of the initiated catalysts of the present invention broadly comprise those described in the prior art. This applies to suitable temperatures, pressures, residence times, diluent materials, moderating agents, and recycle operations, or applying successive conversions in different reactors to increase the yields of ethylene oxide. The use of the present initiated catalysts in ethylene oxidation reactions is in no way limited to the use of specific conditions among those which are known to be effective.

For purposes of illustration only, the following are conditions that are often used in current commercial ethylene oxide reactor units: a gas hourly space velocity (i.e., GHSV) of 1500-10,000 h$^{-1}$, a reactor inlet pressure of 150-400 psig, a coolant temperature of 180-315° C., an oxygen conversion level of 10-60%, and an EO production rate (i.e., work rate) of from about 150 to about 300 Kg ethylene oxide per m$^3$ of catalyst per hour. The feed composition at the reactor inlet may typically comprises 1-40% ethylene, 3-12% $O_2$, 0.3-40% $CO_2$, O-3% ethane, 0.3-20 ppmv total concentration of organic chloride moderator(s), and the balance of the feed being comprised of argon, methane, nitrogen or mixtures thereof.

After the catalyst's initiation period, the feed composition is adjusted to the design of the high selectivity operation. For this stage of the catalyst performance as a high selectivity catalyst, the design conditions typically are:

| Feed Composition | 15-35% | ethylene |
| --- | --- | --- |
| | 4-9% | oxygen |
| | 0.5-6% | Carbon dioxide |
| | 0.5-5.0 ppm | moderator |
| | Balance | Inert gas |
| Ethylene oxide in effluent | 1.4-4% | |
| GHSV | 3500-5000 | |
| Reaction pressure | 250-350 psig | |

For this stage of the catalyst performance as a high selectivity catalyst, the preferred design conditions are:

| Feed Composition | 20-25% | ethylene |
| --- | --- | --- |
| | 5-7% | oxygen |
| | 0.5-2% | Carbon dioxide |
| | 0.5-5.0 ppm | moderator |
| | Balance | Inert gas |
| Ethylene oxide in effluent | 1.6-3% | |
| GHSV | 3500-5000 | |
| Reaction pressure | 250-350 psig | |

The following non-limiting examples serve to illustrate the invention.

EXAMPLE 1

Silver based catalyst preparation and activation followed generally conventional procedures, as disclosed above. Specifically, a 15 Kg portion of alumina support was placed in a flask and evacuated to about 0.1 torr prior to impregnation. To the above silver solution were added aqueous solutions of cesium hydroxide, perrhenic acid, and ammonium sulfate in order to prepare a catalyst composition according to examples 5-10 of U.S. Pat. No. 4,766,105 to Lauritzen et al. After thorough mixing, the promoted silver solution was aspirated into the evacuated flask to cover the carrier while maintaining the pressure at about 0.1 torr. The vacuum was released after about 5 minutes to restore ambient pressure, hastening complete penetration of the solution into the pores. Subsequently, the excess impregnation solution was drained from the impregnated carrier.

Calcination of the wet catalyst was performed on a moving belt calciner. In this unit, the wet catalyst was transported on a stainless steel belt through a multi-zone furnace. All zones of the furnace were continuously purged with pre-heated, nitrogen and the temperature was increased gradually as the catalyst passed from one zone to the next. The heat supplied to the catalyst was radiated from the furnace walls and from the preheated nitrogen. In this example, the wet catalyst entered the furnace at ambient temperature. The temperature was then increased gradually to a maximum of about 450° C. as the catalyst passed through the heated zones. In the last (cooling) zone, the temperature of the now calcined catalyst was immediately lowered to less than 100° C. before it emerged into ambient atmosphere.

The total residence time in the furnace was approximately 45 minutes.

The silver based catalyst was charged into a 32.5 mm reactor tube and was tested with a feed gas mixture that included the following components:
  10% ethylene;
  4% oxygen;
  14% carbon dioxide;
  0.8 parts per million, ethyl chloride (moderator); and balance nitrogen.

The temperature of the reactor was increased gradually up to 245° C. After 100 hours, the carbon dioxide concentration in the feed was lowered to 12% in order to maintain the concentration of ethylene oxide in the effluent at 2.2%. After an additional forty hours of heating at 247° C., the selectivity was 84.0% and the effluent gas contained 2.5% ethylene oxide.

The catalyst was cooled down to 220° C. and then the feed composition was gradually adjusted to the following mixture:
  25% ethylene;

7% oxygen;
2% carbon dioxide;
0.8 parts per million, ethyl chloride (moderator); and balance nitrogen.

Under the aforementioned conditions, the catalyst's performance was:
88.5% selectivity;
228° C. reaction temperature; and
2.2% ethylene oxide in the effluent.

EXAMPLE 2

The same catalyst as in Example 1 was treated with a feed gas mixture that included the following components:
10% ethylene;
4% oxygen;
10% carbon dioxide;
0.8 parts per million, ethyl chloride (moderator); and balance nitrogen.

The temperature of the reactor was increased gradually up to 247° C. After 140 hours the selectivity was 84.5% and the effluent gas contained 2.3% ethylene oxide. The catalyst was cooled down to 220° C. and then the feed composition was gradually adjusted to the following mixture:
15% ethylene;
7% oxygen;
5% carbon dioxide;
0.8 parts per million, ethyl chloride (moderator); and balance nitrogen.

Under these conditions, the catalyst's performance was:
86.5% selectivity;
238° C. reaction temperature; and
2.2% ethylene oxide in the effluent.

While the present invention has been particularly shown and described with respect to preferred embodiments thereof it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A method for epoxidation of ethylene comprising:
contacting a catalyst bed including a silver-based highly selective epoxidation catalyst with a feed gas composition at a first temperature during an initiation period, said feed gas composition including ethylene, oxygen, a moderator and carbon dioxide, said carbon dioxide is present in said feed gas composition in a first concentration of greater than about 6 vol. %;
increasing the first temperature to a second temperature to produce a desired concentration of ethylene oxide;
adjusting the feed gas composition in order to maintain said desired concentration of ethylene oxide while achieving a desired catalyst work rate; and
lowering the second temperature to a third temperature, while simultaneously lowering the carbon dioxide concentration to a second concentration of about 5 vol. % or less.

2. The method of claim 1 wherein said first concentration of carbon dioxide in said feed gas is greater than about 10 vol. %.

3. The method of claim 1 wherein said silver-based highly selective epoxidation catalyst comprises a support, a catalytically effective amount of silver or a silver-containing compound, a promoting amount of rhenium or a rhenium-containing compound, and a promoting amount of one or more alkali metals or alkali-metal-containing compounds.

4. The method of claim 3 wherein said support is essentially alpha-alumina having a surface area from 0.1 to 10 $m^2/g$.

5. The method of claim 3 wherein said catalyst further comprises a promoting amount of one or more Group IIA metal-containing compounds, one or more transition metal-containing compounds, one or more sulfur-containing compounds, one or more fluorine-containing compounds, one or more phosphorus-containing compounds, one or more boron-containing compounds, or combinations thereof.

6. The method of claim 5 wherein the Group IIA metal-containing compound comprises beryllium, magnesium, calcium, strontium, barium or combinations thereof.

7. The process of claim 5 wherein the transition metal-containing compound comprises an element selected from Groups IVA, VA, VIA, VIIA and VIIIA of the Periodic Table of the Elements, or combinations thereof.

8. The method of claim 7 wherein the transition metal-containing compound comprises molybdenum, tungsten, chromium, titanium, hafhium, zirconium, vanadium, thorium, tantalum, niobium or combinations thereof.

9. The method of claim 8 wherein the transition metal-containing compound comprises molybdenum or tungsten or combinations thereof.

10. The method of claim 3 wherein the alkali metal-containing compound comprises lithium, sodium, potassium, rubidium, cesium or combinations thereof.

11. The method of claim 3 wherein the alkali metal-containing compound comprises cesium and lithium.

12. The method of claim 1 wherein said first temperature is from about 180° C. to about 220° C. and said second temperature is from about 230° C. to about 270° C.

13. The method of claim 1 wherein said adjusting the feed composition includes changing the concentration of carbon dioxide or ethylene.

14. The method of claim 1 wherein the carbon dioxide concentration is lowered to a second concentration of about 2 vol. % or less.

* * * * *